(12) United States Patent
Matsuda et al.

(10) Patent No.: US 6,227,658 B1
(45) Date of Patent: May 8, 2001

(54) APPARATUS AND METHOD FOR FORMING THIN FILM USING INK-JET MECHANISM

(75) Inventors: Tetsuo Matsuda, Takasaki (JP); Maria Ronay, Briarcliff Manor, NY (US)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/089,505

(22) Filed: Jun. 3, 1998

(51) Int. Cl.[7] .............................. B41J 2/145; B41J 2/045; B41J 2/17
(52) U.S. Cl. .................. 347/68; 347/40; 347/70; 347/95
(58) Field of Search .................. 347/70, 95, 68, 347/12, 40, 47

(56) References Cited

U.S. PATENT DOCUMENTS

| | | | |
|---|---|---|---|
| 4,511,600 | 4/1985 | Leas | 427/75 |
| 4,668,533 | 5/1987 | Miller | 427/98 |
| 4,717,639 | 1/1988 | Dubin et al. | 430/124 |
| 4,746,935 | * 5/1988 | Allen | 347/47 |
| 4,829,020 | 5/1989 | Drummond et al. | 437/81 |
| 5,114,744 | 5/1992 | Cloutier et al. | 427/96 |
| 5,132,248 | * 7/1992 | Drummond et al. | 437/174 |
| 5,292,548 | 3/1994 | Rainwater | 427/97 |
| 5,377,961 | 1/1995 | Smith et al. | 266/237 |
| 5,424,769 | * 6/1995 | Sakai et al. | 347/70 |
| 5,449,754 | 9/1995 | Nishioka | 530/334 |
| 5,466,575 | 11/1995 | Cozzette et al. | 427/6 |
| 5,474,808 | 12/1995 | Aslam | 427/249 |
| 5,498,444 | 3/1996 | Hayes | 427/162 |
| 5,506,607 | 4/1996 | Sanders, Jr. et al. | 347/1 |
| 5,510,066 | 4/1996 | Fink et al. | 264/40.1 |
| 5,560,543 | 10/1996 | Smith et al. | 239/102.2 |
| 5,594,484 | 1/1997 | Furukawa | 347/95 |
| 5,975,668 | * 11/1999 | Fujii et al. | 347/10 |

* cited by examiner

*Primary Examiner*—John Barlow
*Assistant Examiner*—An H. Do
(74) *Attorney, Agent, or Firm*—Banner & Witcoff, Ltd.

(57) ABSTRACT

A liquid material jetted from a nozzle is supplied onto a surface of the semiconductor substrate with use of an ink-jet mechanism comprising a liquid material receiving section, a driving section and a nozzle section. Since a film material (liquid material) is supplied by an ink-jet method, not only the film material only be supplied to a desired region of the semiconductor substrate surface and a supply to an unnecessary region is prevented, but also a variation of a film thickness comes not to be dependent on a pattern on the semiconductor substrate. Therefore, in forming a thin film on a semiconductor substrate, a thin film formation is realized so that utilization efficiency of a film material is increased with reduction in loss thereof and a variation of a thickness of the film formed is not influenced by a pattern on the semiconductor substrate.

15 Claims, 5 Drawing Sheets

APPARATUS AND METHOD FOR FORMING THIN FILM USING INK-JET MECHANISM

BACKGROUND OF THE INVENTION

The present invention relates to an apparatus and method for forming a thin film and more particularly, to an apparatus and method for forming a thin film using an ink-jet mechanism.

Conventionally, various methods for forming a thin film have been proposed in thin film formation of an LSI semiconductor device. As one of conventionally general methods in a field of an LSI semiconductor device, there is named a CVD (Chemical Vapor Deposition) method. As another method, an SOG (Spin-On-Glass) method has also been used widely. These conventional methods are, however, not efficient, since an utilization efficiency of a film material is as low as about in the range of 5 to 20% and a majority of fed material is lost. Such a situation is specially problematic in the case where an expensive material is used as a material for forming a film. In a conventional method, a variation in thickness of a film formed is determined strictly by a pattern on a semiconductor substrate.

In a CVD method, a film thickness is dependent on a pattern density and it tends to be thinner in a higher density region. In an SOG method, a thickness of a formed film is dependent on a flow related with a viscosity of a film material and it is thinner in a broader region than in a narrower region. A control with flexibility on a semiconductor substrate is effective for executing process integration. For example, to form a thick film in a larger groove region is effective for obtaining a good planarity with a CMP (Chemical-Mechanical Polishing) method. CVD and SOG methods do not have such a controllability as can be understood from the above description. Moreover, a process tool requires that peripheral portions are free from a bead in order to protect a clamp mechanism from particle production. While, in general, the peripheral portion of a CVD film on a substrate is removed by 3 to 6 mm from the edge, this removal requires coating with photoresist, etching for removal of the film and other additional process steps including separation of the photoresist for removal of the peripheral bead, which causes a cost to be increased.

As mentioned above, in a conventional method for forming a thin film, there have been problems that utilization efficiency of a film material is low and a great amount of the material comes to be lost useless, a variation of a film thickness formed is severely determined by a pattern on a semiconductor substrate and additional process steps, which increase a cost, are necessary.

BRIEF SUMMARY OF THE INVENTION

The present invention has been made in light of such circumstances and it is an object of the present invention to provide an apparatus and method for forming a thin film, which is high in utilization efficiency of a film material, in which a variation of a film thickness formed is not determined by a pattern on a semiconductor substrate, and which minimizes increase in cost.

In order to achieve the above mentioned object, an apparatus for forming a thin film using an ink-jet mechanism according to a first aspect of the present invention comprises: a plate member with at least one row of plural nozzles arranged in a row; a receiving room for receiving a liquid material; a pressure room for keeping the liquid material supplied from the receiving room in a pressurized condition; a communicating hole communicating with a nozzle; and a driving section, wherein the pressure room is pressurized and thereby the liquid material in the pressure room is jet from the nozzle through the communicating hole by the driving section. In the thin film forming apparatus according to the first aspect of the present invention, the driving section may comprise plural driving elements provided in a corresponding manner to the plural nozzles. In the thin film forming apparatus according to the first aspect of the present invention, a driving element may be an piezoelectric element. In the thin film forming apparatus according to the first aspect of the present invention, a moving device for moving the plate member may be further provided.

An apparatus for forming a thin film using an ink-jet mechanism according to a second aspect of the present invention comprises: a plate member with at least one row of plural nozzles arranged in a row; a receiving portion having a receiving room for receiving a liquid material, a pressure room for keeping the liquid material supplied from the receiving room in a pressurized condition, and a communicating hole communicating with a nozzle, wherein an upper potion is sealed by the plate member; a driving section, wherein the pressure room is pressurized and thereby the liquid material in the pressure room is jetted from a nozzle through the communicating hole by the driving section. In the thin film forming apparatus according to the second aspect of the present invention, the driving section may comprise plural driving elements provided in a corresponding manner to the plural nozzles in plural rows. In the thin film forming apparatus according to the second aspect of the present invention, a driving element may be an piezoelectric element. In the thin film forming apparatus according to the second aspect of the present invention, a moving device for moving the plate member may be further provided.

A method for forming a thin film using an ink-jet mechanism according to a third aspect of the present invention comprises the steps of: disposing a surface of a semiconductor substrate in such a manner that the surface is opposed to a nozzle array of an ink-jet head having at least one row of plural nozzles arranged in a row; and forming a film on a surface of the semiconductor substrate by jetting the liquid material from selected nozzles among the plural nozzles in the at least one row. In the thin film forming method according to the third aspect of the present invention, an atmosphere between a surface of a semiconductor substrate and a nozzle may be a part of a jetting liquid material, for instance, solvent of liquid material can be used to prevent a jet from drying. Similar solvent can be used also as substitution. In the thin film forming method according to the third aspect of the present invention, the step of jetting the liquid material may be a step of driving elements corresponding to selected nozzles among the plural driving elements arranged in a corresponding manner to the plural nozzles of at least one row. In the thin film forming method according to the third aspect of the present invention, a driving element may be a piezoelectric element.

A method of forming a thin film according to a fourth aspect of the present invention comprises the steps of: disposing a surface of a semiconductor substrate in such a manner that the surface of the semiconductor substrate is opposed to a nozzle array of an ink-jet head having plural rows of plural nozzles arranged in rows; and forming a film of a predetermined pattern on the surface of the semiconductor substrate by jetting the liquid material from nozzles selected from the plural nozzles. In the thin film forming method according to the fourth aspect of the present invention, the step of jetting may be a step of driving elements corresponding to selected nozzles among the plural driving elements arranged in a corresponding manner to the plural nozzles of plural rows. In the thin film forming method according to the fourth aspect of the present invention, a driving element may be a piezoelectric element. In the thin film forming method according to the fourth aspect of the present invention, different kinds of liquid material may be jetted from nozzles of respective different rows. In the thin film forming method according to the fourth aspect of the present invention, a liquid material may be an SOG material. In the thin film forming method according to the fourth aspect of the present invention, a liquid may be a dopant. In the thin film forming method according to the fourth aspect of the present invention, a liquid may be a solvent for adjusting a viscosity of a film to be formed. In the thin film forming method using an ink-jet mechanism according to the fourth aspect of the present invention, in the step of forming the film, the nozzle array may be positioned above the surface of the semiconductor substrate and the liquid material may be jetted onto the surface of the semiconductor substrate from the selected nozzles. In the thin film forming method using an ink-jet mechanism according to the fourth aspect of the present invention, in the step of forming the film, the nozzle array may be moved over the surface of the semiconductor substrate and stopped at selected positions, and the liquid material may be jetted onto the surface of the semiconductor substrate from the selected nozzles at the selected positions, while the selected nozzles are changed in accordance with the movement of the nozzle array. In the thin film forming method using an ink-jet mechanism according to the fourth aspect of the present invention, in the step of the different kinds of liquid material may be different kind of dopant.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinbefore.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Embodiments of the present invention will be described below in reference to the accompanying drawings.

Film formation according to the present invention is dependent on a printing technique using an ink-jet method.

Figure 1:
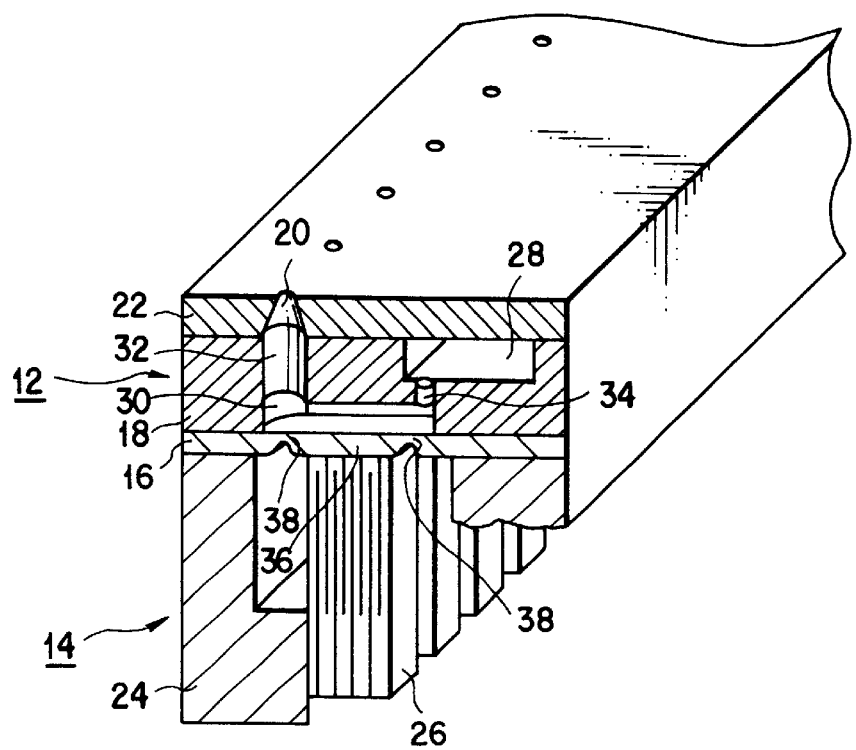
FIG. 1 is a perspective view showing a fundamental construction of an apparatus for forming a thin film comprising an ink-jet mechanism according to an embodiment of the present invention.

FIG. 1 is a sectional view showing a fundamental construction of an typical ink-jet head of an apparatus for forming a thin film according to an embodiment of the present invention including a partially sectional view. The ink-jet head comprises a liquid material receiving section 12 in which a liquid material to be jet is received and a liquid material driving section 14 in which a driving force driving the liquid material is produced, and which is located under the liquid material receiving section 12. As a liquid material, an SOG material, a low melting point material or a liquid comprising a solid material to be deposited and a solvent is used. A partitioning plate member 16 is inserted between the liquid material receiving section and the liquid material driving section to screen from each other.

The liquid material receiving section is constructed from a frame body 18 and a ceiling plate member 22 in which plural nozzle holes 20 are formed in a row covers the upper surface in a sealing manner. The liquid material driving section is also constructed in a similar manner to the liquid material receiving section from a frame body 24, and in the frame body 24, plural piezoelectric members with a multi-layered structure 26 producing a liquid material driving force is arranged in plural rows in the same direction as that of the nozzle holes. The liquid material receiving section has communicating holes 32 communicating between the liquid material receiving room 28 receiving the liquid material and the liquid material pressure room 30 in which the liquid material is pressurized, and between the liquid material pressure room 30 and nozzle holes in the ceiling plate member.

A liquid material supply control valve 34 is provided between the liquid material receiving room and the liquid material pressure room.

Plural nozzle hole are, as mentioned above, disposed in the ceiling plate member in rows. That is, they assume a form of a multi-nozzle type. Thereby, a long thin film forming region can be covered. That is, since plural nozzles are formed in an arrangement in rows, a jet width of a liquid material is broad and therefore a long thin film can be formed with ease. According to the current technique, a dot pitch can be increased to the order of 1000 dpi (1000 dots/inch=25 µm pitch). This resolution is high enough to solve the conventional problems mentioned above.

Figure 2:
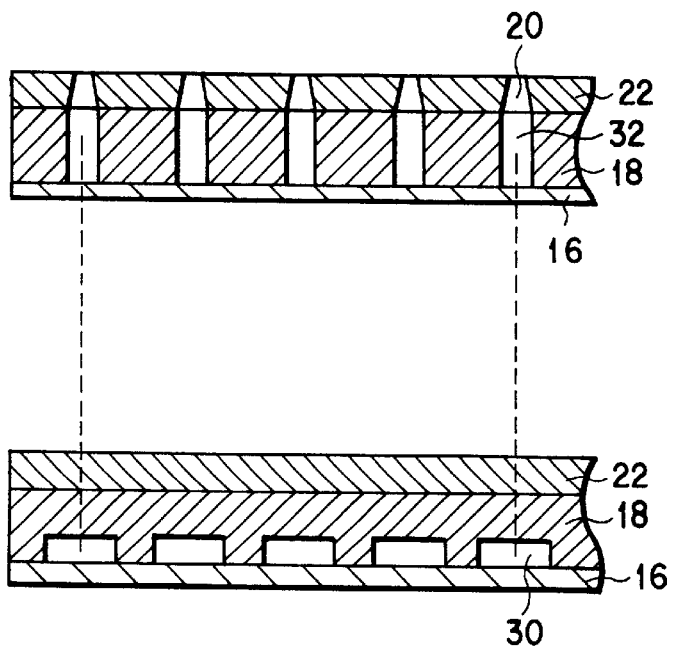
FIG. 2 is a sectional view of communicating holes and a liquid material pressure room in the apparatus for forming a thin film of FIG. 1 taken especially along a direction of arrangement of communicating holes.
Figure 3:
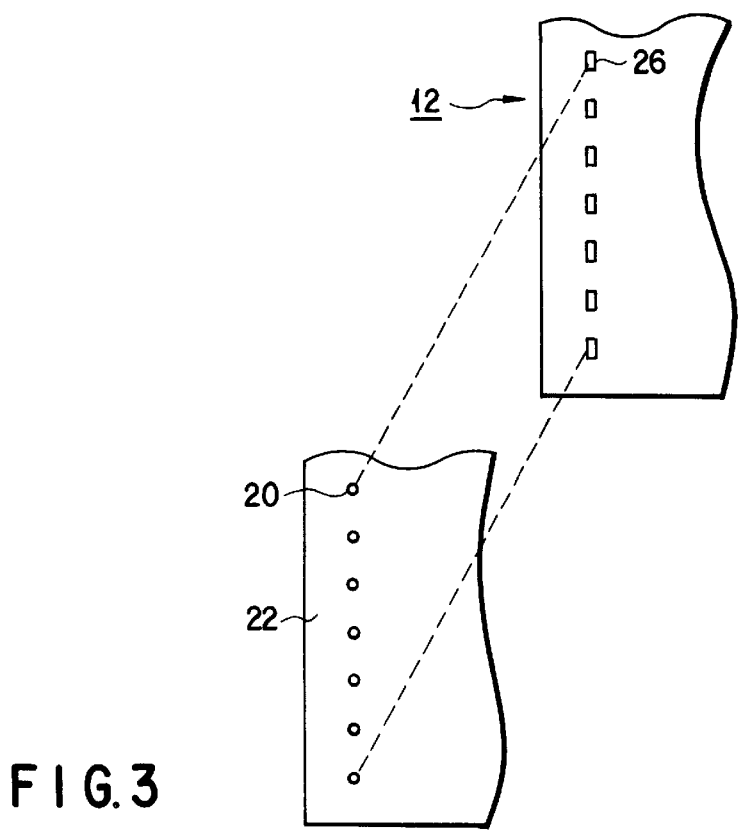
FIG. 3 is a plan view showing a configuration of piezoelectric members having multi-layered structure and nozzle holes inside a liquid driving section in the apparatus for forming a thin film of FIG. 1, wherein the piezoelectric member and the nozzle holes are shown in a corresponding manner.

The liquid material receiving room and plural communicating holes are, as shown in FIG. 2, provided in a corresponding manner to nozzle holes along a direction of arrangement of the nozzle holes. In a similar manner and as shown in FIG. 3, plural piezoelectric members each having a multi-layered structure in the liquid material driving section are disposed in plural rows in a corresponding manner to the nozzle holes along a direction of arrangement of the nozzle holes.

The upper surface of a piezoelectric member contacts with the lower surface of the ceiling plate member, as shown in FIG. 1 and portions 38, disposed along the direction of arrangement of the nozzle holes, on the both edges of a portion 36 (contacting portion) with which an piezoelectric member 26 contacts have a smaller thickness in a sectional profile of a concavity. The liquid material receiving room in the liquid material receiving section is located in an upper portion on one side thereof (on the right side portion as viewed on the sheet on which FIG. 1 is depicted) and the liquid material pressure room is disposed at the bottom of the middle portion of the liquid material receiving section. The communicating holes are located on the other side (on the left side as viewed) of the liquid material receiving section and they extend from the liquid material pressure room to a nozzle hole. The liquid material pressure room is located on the portion (contacting portion) of the partitioning plate member with which a piezoelectric member contacts. Thereby, an piezoelectric member is driven to vibrate under application of a voltage V. When the piezoelectric member vibrates, the above mentioned contacting portion of the partitioning plate member receives a pressure to push up the contacting portion. As a result, the liquid material pressure room, which is located on the contacting portion, receives a pressure to be compressed. Thereby, the liquid material in the liquid material pressure room is supplied to a nozzle hole through a communicating hole and further it is jet to the outside from the nozzle hole. At this point, the liquid material supply control valve is closed to prevent a reverse current of the liquid material back to the liquid material receiving room and at the same time, a pressure caused by drive of piezoelectric members is prevented from leaking to the liquid material receiving room by the closure of the valve. Thereafter, when a supply of voltage to the piezoelectric members is ceased to be disabled, the contacting portion of the partitioning plate member is returned to its initial position, so that a pressure to the liquid material receiving room disappears. Thereby, a supply of the liquid material in the liquid material pressure room to nozzle holes through communicating holes is terminated and a stream jetted from the nozzle holes to the outside disappears. When a pressure to the liquid material is extinct, the liquid material supply control valve, which has been closed, is opened and the liquid material in the liquid material receiving room is made to flow into the liquid material pressure room. In this condition, when a predetermined voltage is again applied to the piezoelectric members, the liquid material in the liquid material pressure room is again jetted to the outside through nozzle holes after the above mentioned operations.

Figure 4:
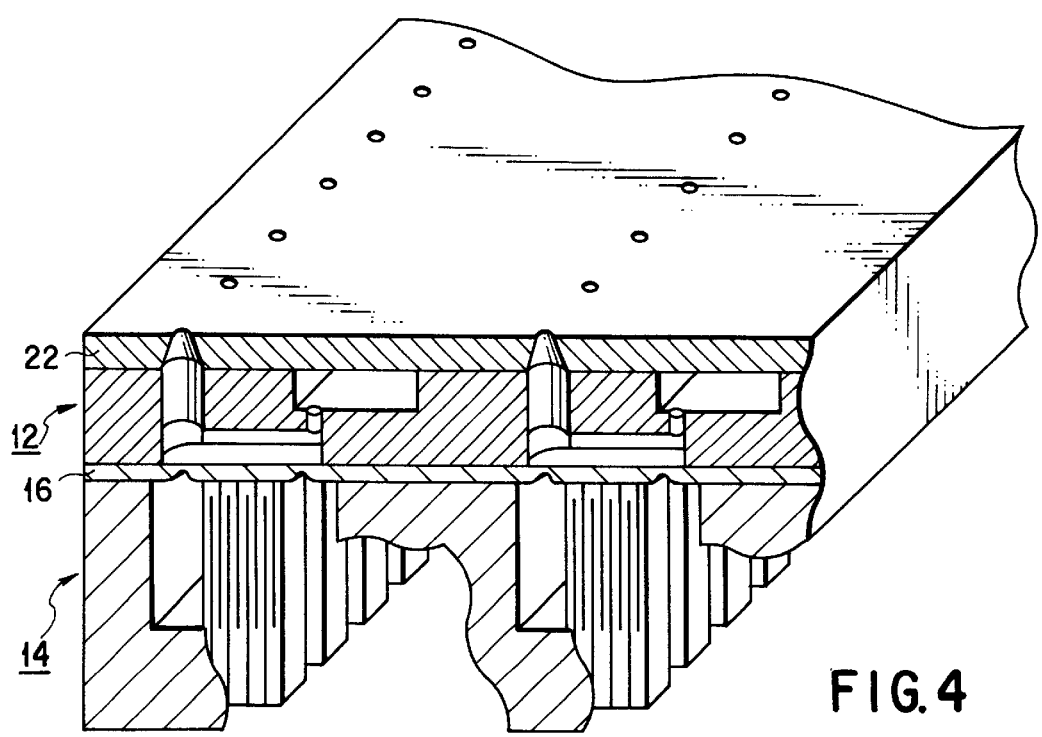
FIG. 4 is a perspective view showing a construction when plural fundamental constructions of an apparatus for forming a thin film of FIG. 1 are arranged in an array.

FIG. 4 shows an example of a nozzle array of an ink-jet head in which plural nozzles each shown in FIG. 1 are arranged in plural rows (two rows are shown in FIG. 4) in an array manner. In the case where an array configuration is employed, a larger region, in which a broader film is formed, can be covered. That is, since plural nozzles are arranged in an array, a jetting width of the liquid material is broad and thus a broad film can be formed.

According to the above mentioned construction, since the liquid material can be supplied to a limited region, a utilization efficiency of the liquid material is extremely high.

Figure 5:
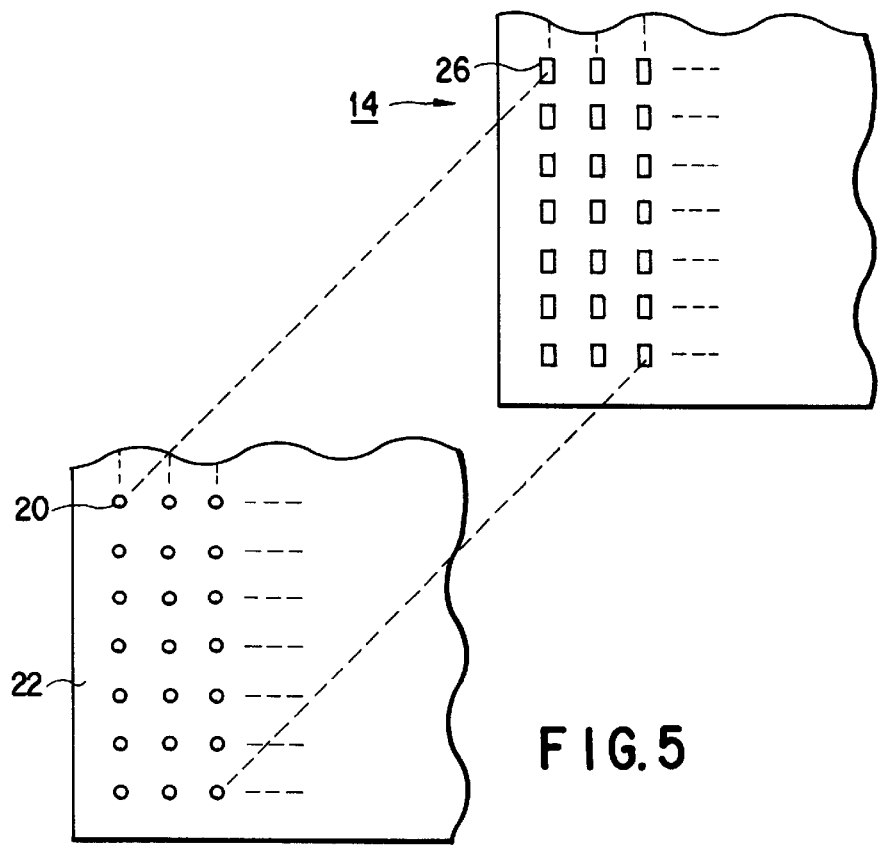
FIG. 5 is a plan view showing a configuration of piezoelectric members having multi-layered structure and nozzle holes inside a liquid driving section in the apparatus for forming a thin film of FIG. 4, wherein the piezoelectric members and the nozzle holes are shown in a corresponding manner.

FIG. 5 is a plan view similar to that in FIG. 3 in the case where plural nozzles are arranged in plural rows and there is shown a condition where piezoelectric members in the liquid material driving section are arranged in plural rows along a direction of arrangement of nozzle holes in a corresponding manner with the nozzle holes.

The case where an insulating film is formed on a semiconductor with use of the apparatus will be described in reference to FIG. 6.

Figure 6:
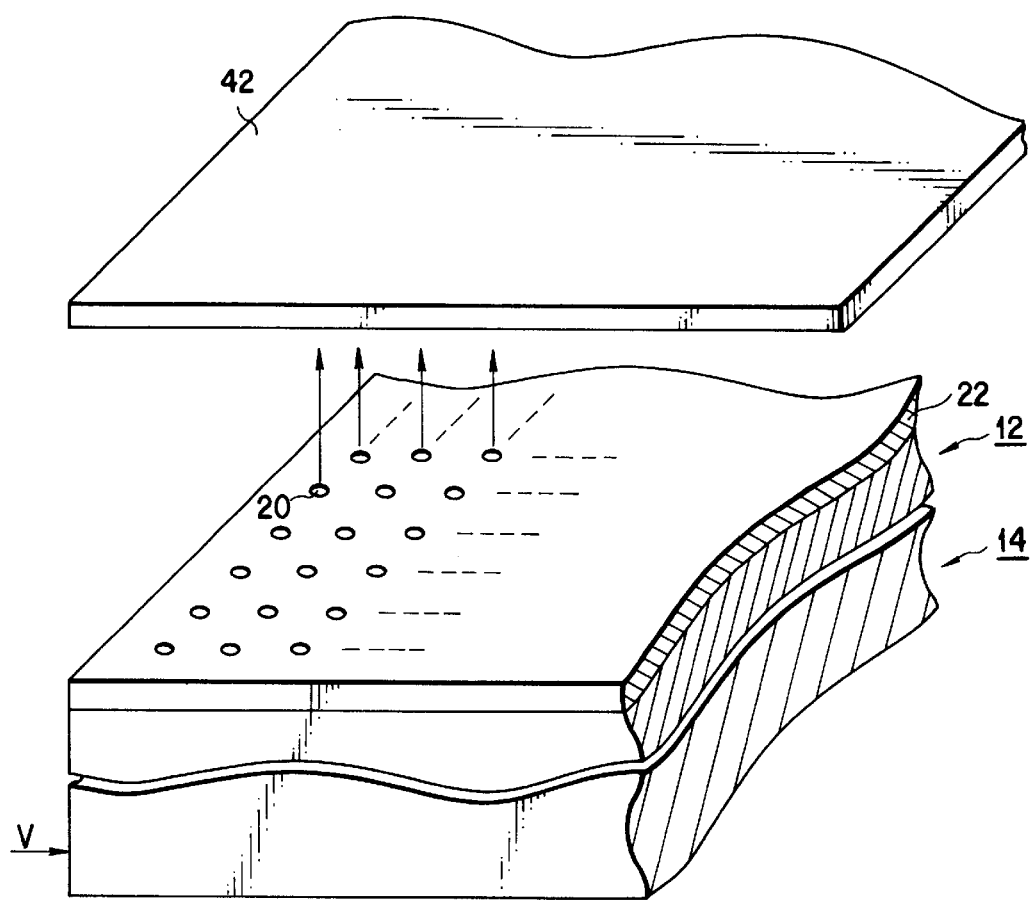
FIG. 6 is a perspective view showing a condition in which an apparatus for forming a thin film comprising an ink-jet mechanism is disposed in an opposed position to a semiconductor substrate.

As shown in FIG. 6, a semiconductor substrate 42 is disposed in a facing manner with a surface of a nozzle array (ceiling plate member 22). If a Pb (lead) layer with a predetermined pattern is to be formed on a surface of the semiconductor substrate, Pb is charged in the liquid material room from a charging port (not shown). Subsequently, a position of the semiconductor substrate is adjusted relative to the nozzle positions. A voltage is applied to the piezoelectric members to be driven, a pressure is given to the liquid material pressure room, thereby the liquid material Pb in the liquid material pressure room is jetted on the surface of the semiconductor substrate from the nozzles. With the current technique, a dot pitch can be increased to the order of 1000 dpi (1000 dot/inch=25 µm pitch), which resolution is satisfactorily high.

Figure 7:
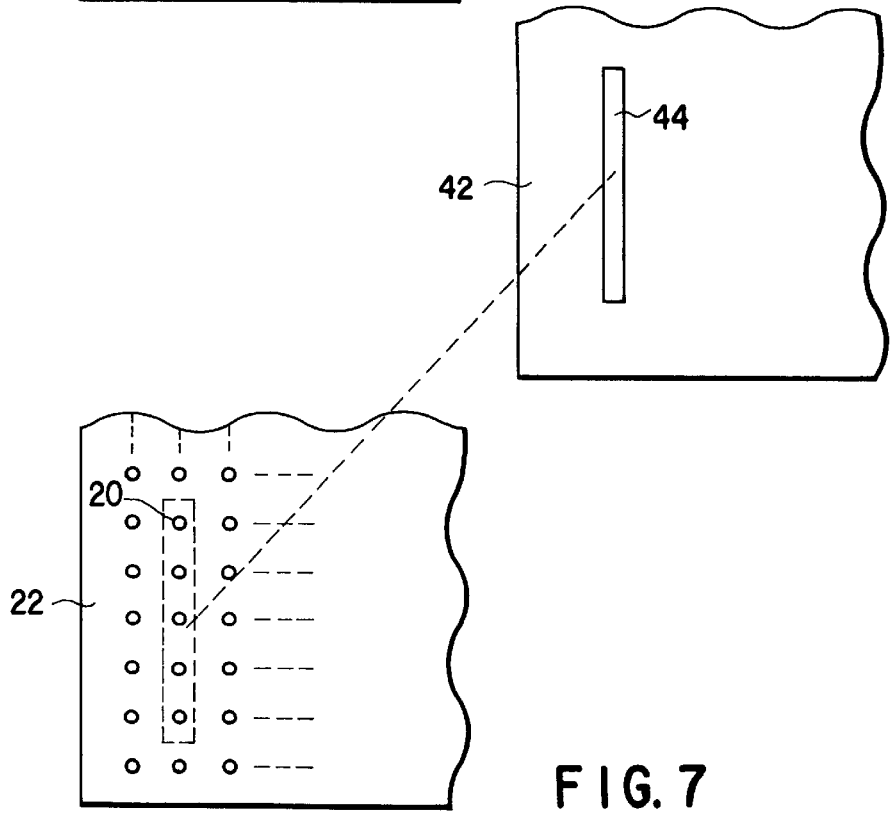
FIG. 7 is a plan view showing selected nozzle holes and a film to be formed on a semiconductor substrate in a corresponding manner.

When the liquid material Pb is jetted from the nozzles, the nozzles are selected among plural nozzles so that a Pb layer having a predetermined pattern on the surface of the semiconductor substrate may be formed. Then, the piezoelectric members are selected among plural piezoelectric members so as to correspond to the pattern. This is to select nozzles for a region corresponding to the pattern. For example, in the case where a shape of a Pb layer pattern (thin film pattern) 44 is a linear shape with a length, as shown in FIG. 7, piezoelectric members are selected so that nozzles included in a region (a region encircled with a broken line) corresponding to the pattern are selected. Moreover, a voltage to be applied to piezoelectric members are selected in accordance to a thickness of a Pb patterned layer and thus a jetting power of nozzles are properly adjusted. This is to set a thickness of the Pb layer to a desired value. Moreover, a distance between the nozzle surface and the surface of the semiconductor substrate is selected according to a scale of the pattern of the Pb layer as well. This is to adjust a degree of a spread of the Pb material jetted from the nozzles according to the scale of the Pb layer to be formed. For example, if a scale of a Pb layer to be formed is larger, a distance is larger and on the other hand, if a scale of a Pb layer to be formed is smaller, a distance is adjusted to be smaller. A Pb film with a desired thickness can be formed in a pattern by adjusting a spread of Pb and a pitch of dots in an arbitrary manner.

According to the above mentioned embodiment, since an ink-jet method is adopted, a liquid material can be supplied to a limited region and a utilization efficiency of the liquid material can be extremely increased. Since an ink-jet method is adopted, a thickness of a film formed on a semiconductor substrate is not influenced by a pattern so as to be dispersed. In addition, since there is no need for additional process steps, increase in cost is not invited. Since an ink-jet method is adopted, a dot pitch can be raised to the order of 1000 dpi (1000 dots/inch=25 µm) and thus a pattern with high resolution can be obtained. Besides, since a liquid material blown onto the surface of a semiconductor substrate flows by its viscosity, a surface of a layer thus formed becomes flat. In the case where a thin film forming treatment is a final treatment, a high temperature treatment can be conducted in the process step by in advance heating the semiconductor substrate. A heating may be applied after a pattern is formed as well.

The present invention is not limited to the above mentioned embodiments, however, for example, an environmental control (for atmospheric layer, temperature or the like) may be conducted so that a liquid material is prevented from drying. It is effective to keep the environment to the same as an atmosphere, in which a solvent in a liquid material is included, from a view point of preventing particles of a liquid material from drying. A pattern recognizing apparatus may be used to decide whether or not a pattern on a substrate coincides with a pattern to be formed. Plural kinds of liquid materials can be added to the ink-jet head. This is a feature which an ink-jet method having a multi-nozzle arrays can enjoy. A nozzle array has, for example, a repeating pattern and can accommodate different liquid materials, such as a liquid A, a liquid B and a liquid C. In this case, the liquid A may be an SOG material, the liquid material B may be a dopant and the liquid material C may be only a solvent useful for control of a viscosity as a characteristic of a film to be formed.

Moreover, a voltage to be applied to piezoelectric members may be changed in order change a quantity of a liquid material jetted from nozzles in a controlling manner.

The nozzle array can accommodate further different dopants and these dopants can be jetted from nozzles of different rows. Alternatively, these dopants are mixed together and the mixed dopant may be jetted from nozzles of one row or different rows.

Figure 8:
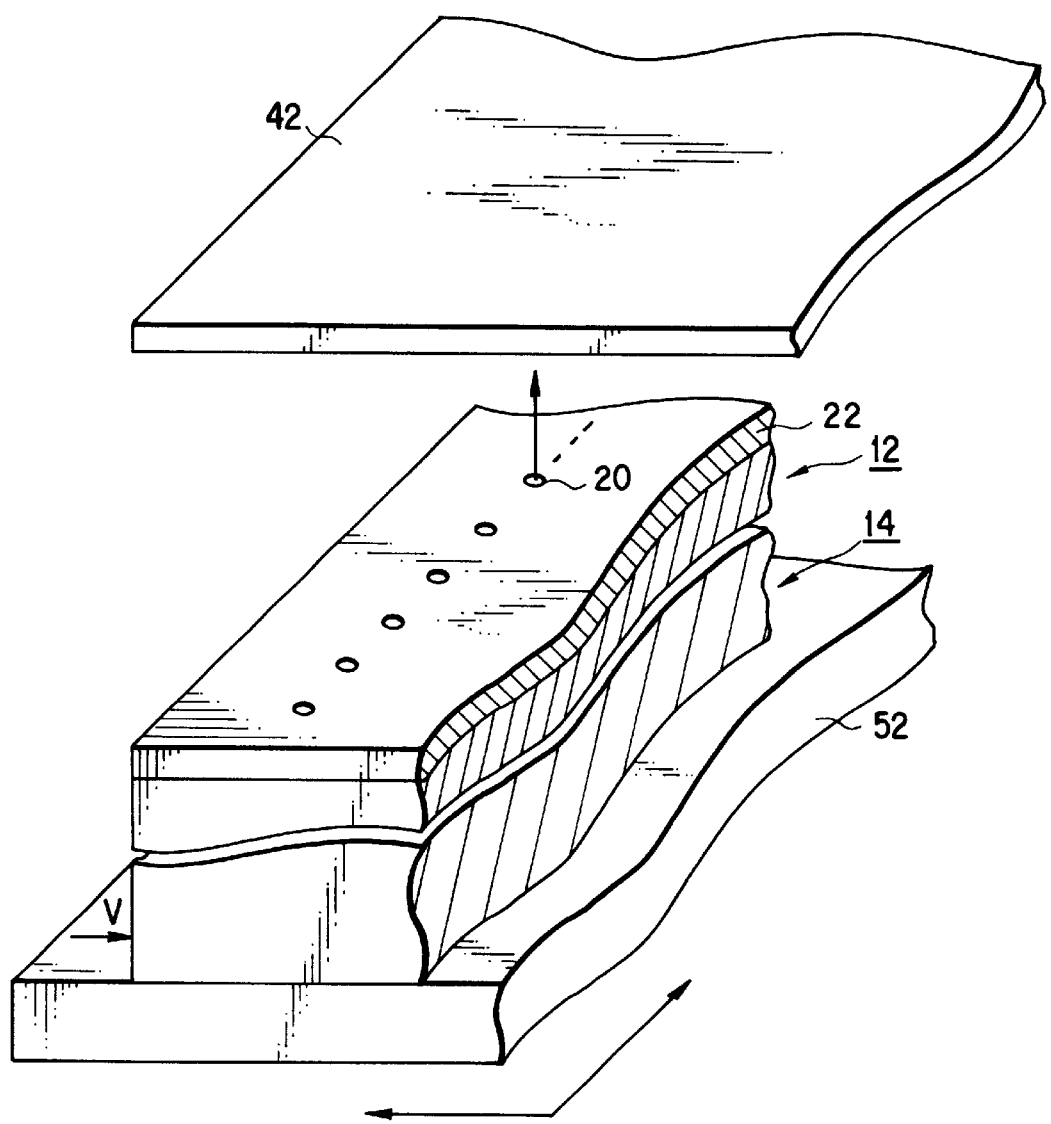
FIG. 8 is a perspective view showing a condition in which an apparatus for forming a thin film comprising an ink-jet mechanism is disposed in an opposed position to a semiconductor substrate.

The ink-jet head apparatus may comprise a moving device 52 driven by a driver (not shown) for moving the nozzle array, i.e., in fact, the ink-jet head, over the semiconductor substrate, as shown in FIG. 8. In this case, as shown in FIG. 8, even when the nozzle array has, for example, a single row of the plural nozzles, a desired film pattern can be formed on the semiconductor substrate, by moving the nozzle array in directions indicated by arrows over the semiconductor substrate, stopping the nozzle array at the desired positions, and jetting a liquid material from the selected nozzles onto the semiconductor substrate at the positions. With the sequence being repeated, a film of a desired pattern can be formed on the surface of the semiconductor substrate.

According to the present invention, since a thin film is formed by an ink-jet method, a film material can be supplied only to a designated region and thereby a utilization efficiency is high, so that a film can be formed with no inconvenience that a disperse of a thickness of a film formed is determined by a pattern on the surface of a semiconductor substrate.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for forming a thin film using an ink-jet mechanism comprising the steps of:

disposing a surface of a semiconductor substrate in such a manner that the surface is opposed to a nozzle array of an ink-jet head having plural rows of plural nozzles; and forming a film on the surface of the semiconductor substrate by jetting plural liquid materials from selected nozzles among the plural nozzles in plural rows, at least one of the liquid materials being a solvent for control of a viscosity of the film to be formed.

2. A method for forming a thin film using an ink-jet mechanism according to claim 1, wherein the step of jetting is a step of driving elements corresponding to selected nozzles among the plural driving elements arranged in a corresponding manner to the plural nozzles of plural rows.

3. A method for forming a thin film using an ink-jet mechanism according to claim 2, wherein a driving element is a piezoelectric element.

4. A method for forming a thin film using an ink-jet mechanism according to claim 1, wherein different kinds of liquid material are jetted from nozzles of respective different rows.

5. A method for forming a thin film using an ink-jet mechanism according to claim 4, wherein a liquid material is an SOG material.

6. A method of forming a thin film using an ink-jet mechanism according to claim 4, wherein the different kinds of liquid material are different kinds of dopant.

7. A method for forming a thin film using an ink-jet mechanism according to claim 4, wherein a liquid is a dopant.

8. A method for forming a thin film using an ink-jet mechanism according to claim 4, wherein a liquid is a solvent for adjusting a viscosity of a film to be formed.

9. A method of forming a thin film using an ink-jet mechanism according to claim 1, wherein, in the step of forming the film, the nozzle array is positioned above the surface of the semiconductor substrate and the liquid material is jetted onto the surface of the semiconductor substrate from the selected nozzles.

10. A method of forming a thin film using an ink-jet mechanism according to claim 1, wherein, in the step of forming the film, the nozzle array is moved over the surface of the semiconductor substrate and stopped at selected positions, and the liquid material is jetted onto the surface of the semiconductor substrate from the selected nozzles at the selected positions, while the selected nozzles are changed in accordance with the movement of the nozzle array.

11. The method according to claim 1, wherein, in said forming step, the rows of nozzles is at least three.

12. A method for forming a thin film using an ink-jet mechanism, comprising the steps of:

disposing a surface of a semiconductor substrate in such a manner that the surface is opposed to a nozzle array of an ink-jet head having at least one row of plural nozzles; and forming a film on a surface of the semiconductor substrate by jetting plural liquid materials from selected nozzles among the plural nozzles in the at least one row, wherein an atmosphere between the surface of the semiconductor substrate and a nozzle of said nozzles is a part of a jetting liquid material, and at least one of the liquid materials is a solvent for control of a viscosity of the film to be formed.

13. The method according to claim 12, wherein said ink-jet head has at least three rows of nozzles.

14. A method for forming a thin film using an ink-jet mechanism, comprising the steps of:

disposing a surface of a semiconductor substrate in such a manner that the surface is opposed to a nozzle array of an ink-jet head having at least one row of plural nozzles; and forming a film on a surface of the semiconductor substrate by jetting liquid material from selected nozzles among the plural nozzles in the at least one row, wherein temperature between the surface of the semiconductor substrate and a nozzle of said nozzles is controlled when jetting said liquid material.

15. A method for forming a thin film using an ink-jet mechanism according to claim 14, wherein at least one of the liquid materials is a solvent for control of a viscosity of the film to be formed.

* * * * *